(12) United States Patent
Lostetter

(10) Patent No.: US 12,127,930 B2
(45) Date of Patent: *Oct. 29, 2024

(54) STENT GRAFT WITH INTERNAL TUNNELS AND FENESTRATIONS AND METHODS OF USE

(71) Applicant: Bolton Medical, Inc., Sunrise, FL (US)

(72) Inventor: Timothy Lostetter, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 510 days.

This patent is subject to a terminal disclaimer.

(21) Appl. No.: 17/486,564

(22) Filed: Sep. 27, 2021

(65) Prior Publication Data

US 2022/0008191 A1    Jan. 13, 2022

Related U.S. Application Data

(63) Continuation of application No. 16/513,559, filed on Jul. 16, 2019, now Pat. No. 11,154,392, which is a
(Continued)

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2220/0016* (2013.01);
(Continued)

(58) Field of Classification Search
CPC ................ A61F 2/856; A61F 2002/065; A61F 2002/067; A61F 2002/068; A61F 2/06; A61F 2/07; A61F 2002/061

See application file for complete search history.

(56) References Cited

U.S. PATENT DOCUMENTS

| 4,501,263 A | 2/1985 | Harbuck |
| 5,123,917 A | 6/1992 | Lee |

(Continued)

FOREIGN PATENT DOCUMENTS

| CN | 201230914 Y | 5/2009 |
| CN | 101601618 A | 12/2009 |

(Continued)

OTHER PUBLICATIONS

"Bolton Medical Thoracic Branch Graft Case Presentation," Charing Cross Symposium Annual Meeting, London, Apr. 8-12, 2011.
(Continued)

*Primary Examiner* — Alvin J Stewart
(74) *Attorney, Agent, or Firm* — Stephen J. Kenny; Foley Hoag LLP

(57) ABSTRACT

A thoraco-abdominal branch graft prosthesis includes a lumen main graft component that defines a lumen and at least one main graft wall fenestration. An open distal end of the main graft component is tapered and has a smaller diameter than the proximal end of the main graft component. At least one tunnel graft component of the branch graft prosthesis defines at least one tunnel graft fenestration. The tunnel graft component is within the main graft lumen defined by the luminal main graft component. A luminal wall of the tunnel graft component is fixed to the luminal wall of the main graft component. The fenestration of the tunnel graft wall is aligned with the fenestration of the main graft wall. The thoraco-abdominal branch graft prosthesis can be implanted in a patient at a site of a thoraco-abdominal aneurysm.

6 Claims, 3 Drawing Sheets

Related U.S. Application Data continuation of application No. 15/478,737, filed on Apr. 4, 2017, now Pat. No. 10,390,932.

(60) Provisional application No. 62/335,284, filed on May 12, 2016, provisional application No. 62/319,434, filed on Apr. 7, 2016, provisional application No. 62/318,447, filed on Apr. 5, 2016.

(52) U.S. Cl.
CPC . *A61F 2220/005* (2013.01); *A61F 2220/0075* (2013.01); *A61F 2250/0026* (2013.01); *A61F 2250/0039* (2013.01)

(56) References Cited

U.S. PATENT DOCUMENTS

| | | | |
|---|---|---|---|
| 5,231,989 | A | 8/1993 | Middleman et al. |
| 5,507,769 | A | 4/1996 | Marin et al. |
| 5,575,817 | A | 11/1996 | Martin |
| 5,683,449 | A | 11/1997 | Marcade |
| 5,755,772 | A | 5/1998 | Evans et al. |
| 5,843,160 | A | 12/1998 | Rhodes |
| 5,855,598 | A | 1/1999 | Pinchuk |
| 5,984,955 | A * | 11/1999 | Wisselink ............... A61F 2/954 623/1.35 |
| 6,059,824 | A | 5/2000 | Taheri |
| 6,171,334 | B1 | 1/2001 | Cox |
| 6,187,033 | B1 | 2/2001 | Schmitt et al. |
| 6,210,429 | B1 | 4/2001 | Vardi et al. |
| 6,280,464 | B1 | 8/2001 | Hayashi |
| 6,306,141 | B1 | 10/2001 | Jervis |
| 6,325,826 | B1 * | 12/2001 | Vardi ...................... A61F 2/915 623/1.35 |
| 6,344,056 | B1 | 2/2002 | Dehdashtian |
| 6,395,018 | B1 | 5/2002 | Castaneda |
| 6,428,565 | B1 * | 8/2002 | Wisselink ................. A61F 2/07 623/1.11 |
| 6,585,756 | B1 | 7/2003 | Strecker |
| 6,592,615 | B1 | 7/2003 | Marcade et al. |
| 6,595,963 | B1 * | 7/2003 | Barbut ............... A61M 1/3653 604/9 |
| 6,645,242 | B1 * | 11/2003 | Quinn ...................... A61F 2/07 623/1.13 |
| 6,676,699 | B2 | 1/2004 | Shiu |
| 7,294,147 | B2 | 11/2007 | Hartley |
| 7,407,509 | B2 | 8/2008 | Greenberg et al. |
| 7,435,253 | B1 | 10/2008 | Hartley et al. |
| 7,438,721 | B2 | 10/2008 | Doig et al. |
| 7,537,606 | B2 | 5/2009 | Hartley et al. |
| 7,550,004 | B2 | 6/2009 | Bahler et al. |
| 7,641,646 | B2 | 1/2010 | Kennedy, II |
| 7,731,744 | B1 | 6/2010 | Cox |
| 7,763,063 | B2 | 7/2010 | Arbefeuille et al. |
| 7,828,837 | B2 | 11/2010 | Khoury |
| 7,854,758 | B2 | 12/2010 | Taheri |
| 7,914,572 | B2 | 3/2011 | Hartley et al. |
| 8,007,605 | B2 | 8/2011 | Arbefeuille et al. |
| 8,021,419 | B2 | 9/2011 | Hartley et al. |
| 8,048,140 | B2 | 11/2011 | Purdy |
| 8,052,736 | B2 | 11/2011 | Doig et al. |
| 8,062,345 | B2 | 11/2011 | Ouellette et al. |
| 8,062,349 | B2 | 11/2011 | Moore et al. |
| 8,070,790 | B2 | 12/2011 | Berra et al. |
| 8,092,511 | B2 | 1/2012 | Chuter |
| 8,105,372 | B1 | 1/2012 | Chuter |
| 8,167,930 | B2 | 5/2012 | Allen et al. |
| 8,172,895 | B2 | 5/2012 | Anderson et al. |
| 8,267,988 | B2 | 9/2012 | Hamer et al. |
| 8,273,115 | B2 | 9/2012 | Hamer et al. |
| 8,292,943 | B2 | 10/2012 | Berra et al. |
| 8,308,790 | B2 | 11/2012 | Arbefeuille et al. |
| 8,333,800 | B2 | 12/2012 | Bruszewski et al. |
| 8,337,546 | B2 | 12/2012 | Bruszewski |
| 8,361,134 | B2 | 1/2013 | Hartley et al. |
| 8,394,136 | B2 | 3/2013 | Hartley et al. |
| 8,449,595 | B2 | 5/2013 | Ouellette et al. |
| 8,474,120 | B2 | 7/2013 | Hagaman et al. |
| 8,500,792 | B2 | 8/2013 | Berra |
| 8,523,934 | B2 | 9/2013 | Purdy |
| 8,545,549 | B2 | 10/2013 | Hartley et al. |
| 8,574,284 | B2 | 11/2013 | Roeder et al. |
| 8,574,288 | B2 | 11/2013 | Hartley et al. |
| 8,636,788 | B2 | 1/2014 | Arbefeuille et al. |
| 8,663,310 | B2 | 3/2014 | Greenberg et al. |
| 8,728,145 | B2 | 5/2014 | Chuter et al. |
| 8,740,963 | B2 | 6/2014 | Arbefeuille et al. |
| 8,740,966 | B2 | 6/2014 | Brocker et al. |
| 8,753,386 | B2 | 6/2014 | Shaw |
| 8,795,349 | B2 * | 8/2014 | Huser ...................... A61F 2/07 623/1.13 |
| 8,808,358 | B2 | 8/2014 | Khoury |
| 8,870,939 | B2 | 10/2014 | Roeder et al. |
| 8,870,946 | B1 | 10/2014 | Quinn |
| 8,940,040 | B2 | 1/2015 | Shahriari |
| 8,945,202 | B2 | 2/2015 | Mayberry et al. |
| 8,945,205 | B2 | 2/2015 | Greenberg |
| 8,992,593 | B2 | 3/2015 | Chuter et al. |
| 8,998,970 | B2 | 4/2015 | Arbefeuille et al. |
| 8,998,971 | B1 | 4/2015 | Kelly |
| 9,034,027 | B2 | 5/2015 | Ivancev |
| 9,101,455 | B2 | 8/2015 | Roeder et al. |
| 9,101,506 | B2 | 8/2015 | Arbefeuille et al. |
| 9,149,382 | B2 | 10/2015 | Greenberg et al. |
| 9,173,755 | B2 | 11/2015 | Berra et al. |
| 9,198,786 | B2 | 12/2015 | Moore et al. |
| 9,220,617 | B2 | 12/2015 | Berra |
| 9,233,015 | B2 | 1/2016 | Geusen et al. |
| 9,259,336 | B2 | 2/2016 | Schaeffer et al. |
| 9,320,631 | B2 | 4/2016 | Moore et al. |
| 9,333,104 | B2 | 5/2016 | Ouellette et al. |
| 9,364,314 | B2 | 6/2016 | Berra et al. |
| 9,408,734 | B2 | 8/2016 | Arbefeuille et al. |
| 9,408,735 | B2 | 8/2016 | Arbefeuille et al. |
| 9,439,751 | B2 | 9/2016 | White et al. |
| 9,463,102 | B2 | 10/2016 | Kelly |
| 9,554,929 | B2 | 1/2017 | Arbefeuille et al. |
| 9,561,124 | B2 | 2/2017 | Arbefeuille et al. |
| 9,592,112 | B2 | 3/2017 | Arbefeuille et al. |
| 9,597,209 | B2 * | 3/2017 | Khoury ................... A61F 2/856 |
| 9,649,188 | B2 | 5/2017 | Hartley |
| 9,655,712 | B2 | 5/2017 | Berra et al. |
| 9,827,123 | B2 | 11/2017 | Arbefeuille et al. |
| 9,855,130 | B2 | 1/2018 | Roeder et al. |
| 9,861,505 | B2 * | 1/2018 | Khoury ................... A61F 2/07 |
| 9,877,857 | B2 | 1/2018 | Arbefeuille et al. |
| 9,907,686 | B2 | 3/2018 | Ouellette et al. |
| 9,913,743 | B2 | 3/2018 | Arbefeuille et al. |
| 9,925,080 | B2 | 3/2018 | Arbefeuille et al. |
| 10,105,248 | B2 | 10/2018 | Berra et al. |
| 10,105,250 | B2 | 10/2018 | Berra |
| 10,390,929 | B2 | 8/2019 | Arbefeuille et al. |
| 10,390,930 | B2 | 8/2019 | Arbefeuille et al. |
| 10,390,932 | B2 * | 8/2019 | Lostetter ................. A61F 2/07 |
| 10,524,893 | B2 | 1/2020 | Parodi et al. |
| 10,646,365 | B2 | 5/2020 | Berra et al. |
| 10,898,357 | B2 | 1/2021 | Arbefeuille et al. |
| 10,918,509 | B2 | 2/2021 | Moore et al. |
| 11,065,100 | B2 | 7/2021 | Parodi et al. |
| 11,154,392 | B2 * | 10/2021 | Lostetter ................. A61F 2/07 |
| 11,395,750 | B2 * | 7/2022 | Lostetter ................. A61F 2/89 |
| 11,446,167 | B2 | 9/2022 | Parodi |
| 11,547,549 | B2 | 1/2023 | Arbefeuille et al. |
| 11,918,451 | B2 | 3/2024 | Parodi et al. |
| 2002/0013620 | A1 | 1/2002 | Kujawski |
| 2002/0052643 | A1 | 5/2002 | Wholey et al. |
| 2002/0062133 | A1 | 5/2002 | Gilson et al. |
| 2002/0156521 | A1 | 10/2002 | Ryan et al. |
| 2003/0109919 | A1 | 6/2003 | Gantt et al. |
| 2003/0120333 | A1 | 6/2003 | Ouriel et al. |
| 2003/0130725 | A1 | 7/2003 | DePalma et al. |
| 2003/0157805 | A1 | 8/2003 | Schultz et al. |
| 2003/0199967 | A1 | 10/2003 | Hartley et al. |

(56) References Cited

U.S. PATENT DOCUMENTS

| | | |
|---|---|---|
| 2003/0204242 A1 | 10/2003 | Zarins et al. |
| 2004/0006299 A1 | 1/2004 | Barbut |
| 2004/0215327 A1 | 10/2004 | Doig et al. |
| 2005/0010277 A1 | 1/2005 | Chuter |
| 2005/0059923 A1 | 3/2005 | Gamboa |
| 2005/0102018 A1 | 5/2005 | Carpenter et al. |
| 2005/0131518 A1* | 6/2005 | Hartley .................. A61F 2/856 623/1.13 |
| 2005/0131523 A1 | 6/2005 | Bashiri et al. |
| 2005/0177222 A1 | 8/2005 | Mead |
| 2006/0095118 A1 | 5/2006 | Hartley |
| 2006/0184228 A1* | 8/2006 | Khoury .................. A61F 2/915 623/1.13 |
| 2006/0229707 A1 | 10/2006 | Khoury |
| 2007/0055350 A1 | 3/2007 | Erickson et al. |
| 2007/0106368 A1 | 5/2007 | Vonderwalde |
| 2007/0135818 A1 | 6/2007 | Moore et al. |
| 2007/0142896 A1 | 6/2007 | Anderson et al. |
| 2007/0168013 A1 | 7/2007 | Douglas |
| 2007/0198078 A1 | 8/2007 | Berra et al. |
| 2007/0203566 A1 | 8/2007 | Arbefeuille et al. |
| 2008/0077226 A1 | 3/2008 | Ouellette et al. |
| 2008/0091260 A1 | 4/2008 | Pomeranz et al. |
| 2008/0109066 A1* | 5/2008 | Quinn ...................... A61F 2/07 623/1.13 |
| 2008/0114444 A1 | 5/2008 | Yu |
| 2008/0147163 A1 | 6/2008 | Allen |
| 2008/0183273 A1 | 7/2008 | Mesana et al. |
| 2008/0264102 A1 | 10/2008 | Berra |
| 2008/0281399 A1 | 11/2008 | Hartley et al. |
| 2009/0012597 A1 | 1/2009 | Doig et al. |
| 2009/0048663 A1 | 2/2009 | Greenberg |
| 2009/0125100 A1 | 5/2009 | Mead |
| 2009/0264988 A1 | 10/2009 | Mafi et al. |
| 2009/0306763 A1 | 12/2009 | Roeder et al. |
| 2009/0319022 A1* | 12/2009 | Hartley .................... A61F 2/07 623/1.13 |
| 2010/0030255 A1 | 2/2010 | Berra et al. |
| 2010/0049298 A1 | 2/2010 | Hamer et al. |
| 2010/0057186 A1* | 3/2010 | West ........................ A61F 2/07 623/1.13 |
| 2010/0234932 A1 | 9/2010 | Arbefeuille et al. |
| 2011/0087318 A1 | 4/2011 | Daugherty et al. |
| 2011/0118821 A1 | 5/2011 | Brocker et al. |
| 2011/0172762 A1 | 7/2011 | Hartley et al. |
| 2011/0208288 A1 | 8/2011 | Arbefeuille et al. |
| 2011/0218607 A1 | 9/2011 | Arbefeuille et al. |
| 2011/0245906 A1 | 10/2011 | DiMatteo et al. |
| 2011/0257731 A1 | 10/2011 | Hartley et al. |
| 2011/0270380 A1 | 11/2011 | Bruszewski |
| 2011/0313503 A1 | 12/2011 | Berra et al. |
| 2012/0089220 A1 | 4/2012 | Lualdi |
| 2012/0123464 A1 | 5/2012 | Rasmussen et al. |
| 2012/0130472 A1 | 5/2012 | Shaw |
| 2012/0158121 A1 | 6/2012 | Ivancev et al. |
| 2012/0245672 A1 | 9/2012 | Arbefeuille et al. |
| 2012/0271401 A1 | 10/2012 | Bruszewski et al. |
| 2012/0296414 A1 | 11/2012 | Hartley |
| 2012/0310324 A1 | 12/2012 | Benary et al. |
| 2013/0013053 A1 | 1/2013 | Hartley et al. |
| 2013/0079870 A1* | 3/2013 | Roeder .................... A61F 2/07 623/1.35 |
| 2013/0138199 A1 | 5/2013 | Ivancev et al. |
| 2013/0184806 A1 | 7/2013 | Arbefeuille et al. |
| 2013/0197627 A1 | 8/2013 | Jensen et al. |
| 2013/0211506 A1 | 8/2013 | Dake et al. |
| 2013/0268059 A1 | 10/2013 | Hagaman et al. |
| 2013/0282103 A1 | 10/2013 | Madjarov et al. |
| 2014/0039597 A9 | 2/2014 | Arbefeuille et al. |
| 2014/0046428 A1 | 2/2014 | Cragg et al. |
| 2014/0135890 A9 | 5/2014 | Berra |
| 2014/0135892 A1 | 5/2014 | Arbefeuille et al. |
| 2014/0135896 A1 | 5/2014 | Arbefeuille et al. |
| 2014/0148890 A9 | 5/2014 | Ouellette et al. |
| 2014/0243952 A1 | 8/2014 | Parodi |
| 2014/0277340 A1 | 9/2014 | White et al. |
| 2014/0277347 A1 | 9/2014 | Daugherty et al. |
| 2014/0277370 A1 | 9/2014 | Brocker et al. |
| 2014/0277379 A1 | 9/2014 | Vogel et al. |
| 2014/0288627 A1 | 9/2014 | Ouellette et al. |
| 2015/0173922 A1 | 6/2015 | Arbefeuille et al. |
| 2015/0202066 A1 | 7/2015 | Berra et al. |
| 2015/0202068 A1 | 7/2015 | Arbefeuille et al. |
| 2015/0209164 A1 | 7/2015 | Kelly |
| 2015/0272755 A1 | 10/2015 | Arbefeuille et al. |
| 2016/0045350 A1 | 2/2016 | Berra |
| 2016/0081787 A1 | 3/2016 | Parodi et al. |
| 2016/0184077 A1 | 6/2016 | Choubey et al. |
| 2016/0184078 A1 | 6/2016 | Choubey et al. |
| 2016/0184115 A1 | 6/2016 | Ondersma et al. |
| 2016/0270901 A1 | 9/2016 | Berra et al. |
| 2016/0270936 A1 | 9/2016 | Berra et al. |
| 2016/0310301 A1 | 10/2016 | Moore et al. |
| 2016/0338867 A1 | 11/2016 | White et al. |
| 2017/0000600 A1 | 1/2017 | Berra et al. |
| 2017/0007392 A1* | 1/2017 | Lourenço ............... A61F 2/856 |
| 2017/0100232 A1 | 4/2017 | Arbefeuille et al. |
| 2017/0100271 A1 | 4/2017 | Arbefeuille et al. |
| 2017/0135807 A1 | 5/2017 | Arbefeuille et al. |
| 2017/0151076 A9 | 6/2017 | Arbefeuille et al. |
| 2017/0165090 A1 | 6/2017 | Arbefeuille et al. |
| 2017/0165091 A1 | 6/2017 | Arbefeuille et al. |
| 2017/0281332 A1 | 10/2017 | Lostetter |
| 2017/0281382 A1 | 10/2017 | Lostetter et al. |
| 2017/0319359 A1 | 11/2017 | Mehta |
| 2017/0340433 A1 | 11/2017 | Berra et al. |
| 2017/0340462 A1 | 11/2017 | Lostetter |
| 2018/0071123 A1 | 3/2018 | Arbefeuille et al. |
| 2018/0078394 A1 | 3/2018 | Zimmerman et al. |
| 2018/0110638 A1 | 4/2018 | Berra et al. |
| 2018/0140448 A1 | 5/2018 | Arbefeuille et al. |
| 2018/0206972 A1 | 7/2018 | Arbefeuille et al. |
| 2019/0192324 A1 | 6/2019 | Moore et al. |
| 2019/0328557 A1* | 10/2019 | Lostetter ................. A61F 2/856 |
| 2020/0085560 A1 | 3/2020 | Parodi et al. |
| 2021/0307895 A1 | 10/2021 | Parodi et al. |
| 2022/0008191 A1 | 1/2022 | Lostetter |
| 2022/0313459 A1 | 10/2022 | Lostetter |
| 2023/0102994 A1 | 3/2023 | Parodi |

FOREIGN PATENT DOCUMENTS

| | | |
|---|---|---|
| CN | 102379757 A | 3/2012 |
| CN | 102488575 A | 6/2012 |
| CN | 102641164 A | 8/2012 |
| CN | 103876860 A | 6/2014 |
| CN | 203841852 U | 9/2014 |
| CN | 104287871 A | 1/2015 |
| CN | 102973303 B | 2/2015 |
| CN | 104367400 A | 2/2015 |
| CN | 104546221 A | 4/2015 |
| CN | 105030373 A | 11/2015 |
| EP | 1487380 B1 | 2/2008 |
| EP | 2051663 B1 | 11/2009 |
| EP | 2139429 B1 | 6/2011 |
| EP | 1765222 B1 | 10/2012 |
| EP | 2410945 B1 | 11/2012 |
| EP | 1983933 B1 | 1/2013 |
| EP | 2182889 B1 | 9/2014 |
| EP | 2331013 B1 | 11/2014 |
| EP | 2420206 B1 | 1/2015 |
| EP | 2450006 B1 | 1/2015 |
| JP | 2015519178 A | 7/2015 |
| WO | WO-2001/032103 A1 | 5/2001 |
| WO | WO-2002/038085 A1 | 5/2002 |
| WO | WO-2003/082153 A2 | 10/2003 |
| WO | WO-2005/023149 A2 | 3/2005 |
| WO | WO-2006/034276 A1 | 3/2006 |
| WO | WO-2006/113501 A1 | 10/2006 |
| WO | WO-2007/092276 A2 | 8/2007 |
| WO | WO-2007/123956 A2 | 11/2007 |
| WO | WO-2008/021557 A1 | 2/2008 |
| WO | WO-2009/020653 A1 | 2/2009 |

(56) References Cited

FOREIGN PATENT DOCUMENTS

| WO | WO-2009/124124 | A1 | 10/2009 |
|---|---|---|---|
| WO | WO-2010/005524 | A2 | 1/2010 |
| WO | WO-2010/024879 | A1 | 3/2010 |
| WO | WO-2010/105195 | A2 | 9/2010 |
| WO | WO-2011/056638 | A1 | 5/2011 |
| WO | WO-2012/051532 | A2 | 4/2012 |
| WO | WO-2013/025727 | A1 | 2/2013 |
| WO | WO-2013/071222 | A1 | 5/2013 |
| WO | WO-2013/074990 | A1 | 5/2013 |
| WO | WO-2013/154749 | A1 | 10/2013 |
| WO | WO-2014/149022 | A1 | 9/2014 |
| WO | WO-2014/172501 | A2 | 10/2014 |
| WO | WO-2015/116715 | A1 | 8/2015 |
| WO | WO-2015/188775 | A1 | 12/2015 |
| WO | WO-2016/049037 | A1 | 3/2016 |
| WO | WO-2017/218474 | A1 | 12/2017 |
| WO | WO-2018/026768 | A1 | 2/2018 |
| WO | WO-2018/031632 | A1 | 2/2018 |

OTHER PUBLICATIONS

Browne et al., "Endovascular and surgical techniques: A fenestrated covered suprarenal aortic stent," Eur J Vasc Endovasc Surg, 18:445-449 (1999).

Chuter et al., "Development of a branched stent-graft for endovascular repair of aortic arch aneurysms," J Endovasc Ther, 10:940-945 (2003).

Chuter et al., "Modular branched stent graft for endovascular repair of aortic arch aneurysm and dissection," J Vasc Surg, 38:859-863 (2003).

Funovics, "Branched endografts for aortic arch aneurysms—How close are we?," CIRSE 2011 Conference, Munich Germany, Session No. 802.3 (Sep. 10-14, 2011).

Funovics, "TEVAR in the ascending aorta: A new frontier for endografting—preliminary results and technology transfer," Focus Meeting, Bolton Medical Inc., Barcelona, Spain (Oct. 2011).

Inoue et al., "Aortic arch reconstruction by transluminally placed endovascular branched stent graft," Circulation, 100(Suppl II):II-316-II-321 (1999).

Inoue et al., "Clinical endovascular placement of branched graft for type B aortic dissection," J Thorac Cardiovasc Surg, 112:1111-1113 (1996).

Inoue et al., "Transluminal endovascular branched graft placement for a pseudoaneurysm: Reconstruction of the descending thoracic aorta including the celiac axis," J Thorac Cardiovasc Surg, 114:859-861 (1997).

International Search Report and Witten Opinion for International Application No. PCT/US2017/025912 dated Jun. 26, 2017.

Kinney et al., "Repair of mycotic paravisceral aneurysm with a fenestrated stent-graft," J Endovasc Ther, 7:192-197 (2000).

Lioupis et al., "Treatment of aortic arch aneurysms with a modular transfemoral multibranched stent graft: Initial experience," European Journal of Vascular and Endovascular Surgery, 43:525-532 (2012).

Martinelli, "Partial ascending aorta and total arch reconstruction with bolton medical branched thoracic endograft," Cardiovascular Surgery Meeting, Bologna, Italy (Nov. 14-15, 2011).

Oderich et al., "Initial experience with the Gore Excluder thoracoabdominal branch endoprosthesis," Supplement to Endovascular Today, 15(3):12-16 (2016).

Ouriel et al., "Branched device to preserve hypogastric arterial flow with thoracoabdominal aneurysm repair," J Vasc Surg, 37:481 (2003).

Simring et al., "Total endovascular repair of the arch: Branched endografting makes it easy," Tecnicas Endovasculares, 14(1):3712-3716 (2011).

Wisselink et al., "Endoluminal Repair of Aneurysms Containing Ostia of Essential Branch Arteries: An Experimental Model," J Endovasc Surg, 6:171-179 (1999).

* cited by examiner

STENT GRAFT WITH INTERNAL TUNNELS AND FENESTRATIONS AND METHODS OF USE

RELATED APPLICATIONS

This application is a continuation of U.S. application Ser. No. 16/513,559, filed Jul. 16, 2019, which is a continuation of U.S. application Ser. No. 15/478,737 filed Apr. 4, 2017, now U.S. Pat. No. 10,390,932, which claims the benefit of U.S. Provisional Application Nos. 62/318,447; filed Apr. 5, 2016, 62/319,434, filed Apr. 7, 2016 and 62/335,284, filed May 12, 2016. The entire teachings of the above applications are incorporated herein by reference.

BACKGROUND

Aortic disease, including aneurysms, penetrating atherosclerotic ulcers and dissections can be life-threatening conditions that occur in different regions of the body. Thoracoabdominal aortic disease generally occurs at the level of the crura of the diaphragm and extends for varying distances proximally, distally or both proximally and distally from the crura. Currently, treatment of thoracoabdominal aortic disease includes, for example, open repair in which the affected portions of the aorta are surgically exposed, or less invasive endovascular repair or hybrid approaches that combine open repair and endovascular treatment. Re-routing of blood vessels that branch from the thoracic and abdominal aorta can be required to maintain perfusion of and prevent damage to organs in the vicinity of the thoracoabdominal disease. Patients undergoing thoracoabdominal aortic repair are, consequently, at high risk for surgical complications.

Therefore, a need exists for new and improved endovascular repair devices and methods to treat thoracoabdominal aortic disease that improve the efficiency and accuracy of endovascular repair and overcome or minimize the above-referenced problems.

SUMMARY OF THE INVENTION

The present invention relates to vascular repair devices and methods of using the vascular repair devices to treat aortic vascular damage, such as vascular damage associated with thoracoabdominal aortic disease, including aneurysms, penetrating atherosclerotic ulcers and dissection.

In an embodiment, the invention is a thoraco-abdominal branch graft prosthesis, comprising a main graft component having a luminal wall defining an open proximal end, an open distal end opposite the open proximal end, a main lumen extending from the open proximal end to the open distal end, and at least one main graft wall fenestration. At least one tunnel graft component has a luminal tunnel graft wall defining, at least in part, a tunnel graft proximal end, a tunnel graft distal end opposite the tunnel graft proximal end, a tunnel graft lumen extending from the tunnel graft proximal end to the tunnel graft distal end, and at least one tunnel graft fenestration in the tunnel graft wall, wherein the tunnel graft component is within the main lumen and a major longitudinal axis of the tunnel graft lumen is substantially aligned with a major longitudinal axis of the main lumen, and wherein the luminal wall of the tunnel graft component is fixed to the luminal wall of the main graft component, whereby the fenestration of the tunnel graft wall is aligned with the fenestration of the luminal wall.

In another embodiment, the invention is a method of implanting a thoraco-abdominal branch graft prosthesis. A thoraco-abdominal branch graft prosthesis is delivered through a blood vessel to a thoraco-abdominal aneurysm site in a patient. The thoraco-abdominal branch graft prosthesis includes i) a main graft component having a luminal wall defining, at least in part, an open proximal end, an open distal end opposite the open proximal end, a main lumen extending from the open proximal end to the open distal end, and at least one main graft wall fenestration; and ii) at least one tunnel graft component having a luminal tunnel graft wall defining a tunnel graft proximal end, a tunnel graft distal end opposite the tunnel graft open proximal end, a tunnel graft lumen extending from the tunnel graft proximal end to the tunnel graft distal end, and at least one tunnel graft fenestration in the tunnel graft wall, wherein the tunnel graft component is within the main lumen and a major longitudinal axis of the tunnel graft lumen is substantially aligned with a major longitudinal axis of the main lumen, and wherein the luminal tunnel graft wall of the tunnel graft component is fixed to the luminal wall of the main graft component, whereby the fenestration of the luminal tunnel graft wall is aligned with the fenestration of the main wall, wherein the at least one main wall fenestration is substantially aligned with at least one branch vessel of the patient at the thoraco-abdominal aneurysm site. At least one branch prosthesis is inserted through at least one main wall fenestration and at least one tunnel graft fenestration within the lumen of the at least one tunnel graft component, the at least one branch prosthesis having an open distal end and an open proximal end. One of the distal end or the proximal end of the at least one branch prosthesis is inserted into at least one branch vessel of the patient at the thoraco-abdominal aneurysm site.

The thoraco-abdominal branch graft prosthesis of the invention has several advantages including, for example, the advantage of providing access by the surgeon from a caudal or cranial position relative to the site of the thoraco-abdominal aneurysm, thereby enabling a surgical approach specific to the patient, including the surgical site, degree of the aneurysm and morphology of side vascular branches.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

The invention is generally directed to prostheses for use in treating vascular disease, such as implantation of the prostheses a site of an aortic aneurysm.

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

A description of example embodiments of the invention follows.

When reference is made herein to a prosthesis to be delivered, or implanted in a patient, such as a vascular repair device, the word "proximal" means that portion of the prosthesis or component of the prosthesis that is closer along the path of flow of blood to the heart of the patient and "distal" means that portion of the prosthesis or component of the prosthesis that is further along the path of flow of blood from the heart of the patient.

When, however, reference is made to a delivery system or a component of a delivery system employed to deliver, or implant a vascular repair device, such as a nose cone or handle of a delivery device, the word, "proximal," as employed herein, means closer to the clinician using delivery system. Likewise, "distal" means, when reference is made to a delivery system or a component of a delivery system, such as a nose cone or handle of a delivery device, further away from the clinician using the delivery system.

For clarity, the word "proximate" means close to as opposed to the meanings ascribed to "proximal" or "distal" as described above with respect to either the vascular repair device or delivery system.

Figure 1:
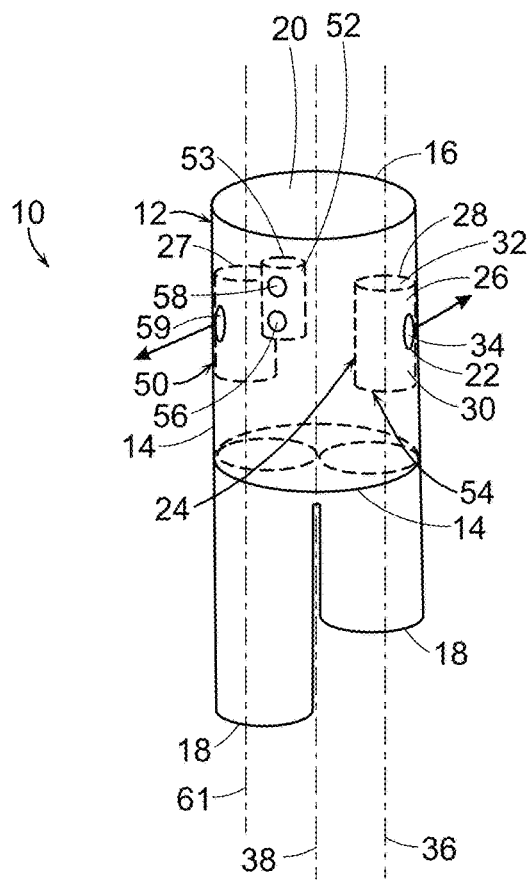
FIG. 1 is a perspective view of one embodiment of a thoraco-abdominal graft prosthesis of the invention.
Figure 2:
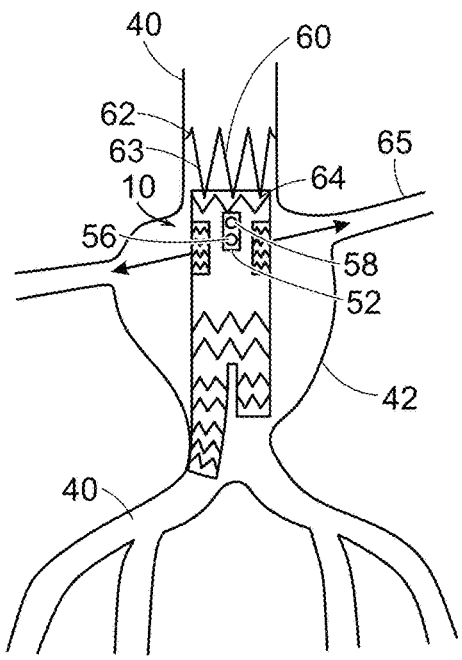
FIG. 2 is a side view of one embodiment of a thoraco-abdominal graft prosthesis of the invention after implantation in a subject.
Figure 3:
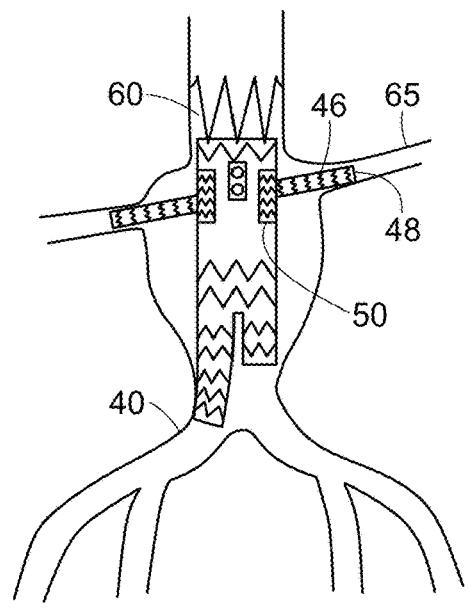
FIG. 3 is a side view of one embodiment of a thoraco-abdominal graft prosthesis and branch prosthesis of the invention after implantation in a subject.

In one embodiment, the thoraco-abdominal branch graft prosthesis is a bifurcated thoraco-abdominal branch graft prosthesis, as shown in FIGS. 1-3. Thoraco-abdominal branch graft prosthesis 10 includes main graft component 12 having luminal wall 14 defining open proximal end 16, at least one open distal end 18 (in the case of a branch graft prosthesis 10, such as a bifurcated graft prosthesis, there are a plurality of distal open ends 18, as shown), opposite open proximal end 16, main lumen 20 extending from open proximal end 16 to open distal end 18, and at least one main graft wall fenestration 22. At least one tunnel graft component 24 has tunnel graft luminal wall 26 defining tunnel graft proximal end 28, tunnel graft distal end 30 opposite tunnel graft proximal end 28, tunnel graft lumen 32 extending from tunnel graft proximal end 28 to tunnel graft distal end 30, and at least one tunnel graft fenestration 34 in tunnel graft luminal wall 26, wherein tunnel graft component 24 is within the main graft lumen 20 and major longitudinal axis 36 of tunnel graft lumen 32 is substantially parallel to major longitudinal axis 38 of the main lumen 20, and wherein tunnel graft luminal wall 26 of tunnel graft component 24 is fixed to luminal wall 14 of main graft component 12, whereby fenestration 34 of tunnel graft luminal wall 26 is aligned with the main graft wall fenestration 22.

As shown in FIGS. 1-3, in an embodiment, thoraco-abdominal branch graft prosthesis 10 includes at least two tunnel graft components 50,54. In one such embodiment, thoraco-abdominal branch graft prosthesis 10 includes three tunnel graft components 50,52,54, wherein tunnel graft components 50,54 are located essentially opposite each other within main lumen 20 of main graft component 12, and wherein fenestrations 34,59 of two tunnel graft components 50,54, respectively, are located at about the same distance from open proximal end 20 of main graft component 12, and wherein third tunnel graft component 52 is at a portion of the main graft component 12 that is between tunnel grafts 50,54, respectively, and wherein open proximal end 53 of third tunnel graft 52 is proximal to open proximal ends 27,29 of tunnel graft components 50,54, respectively. Third tunnel graft component 52 defines two wall apertures 56,58 that are essentially parallel to major longitudinal axis 61 of third tunnel graft component 52, and wherein wall apertures 56,58 are aligned with wall apertures defined by stent graft component 12.

Thoraco-abdominal branch graft prosthesis 10 of the invention can further include bare stent 60 extending proximally from open proximal end 16 of main graft component 12, as shown in FIGS. 2 and 3. Bare stent 60 includes barb 62 proximate to or at at least one of proximal apices 63 of bare stent 62 or distal apices 64 of bare stent 60.

Figure 5:
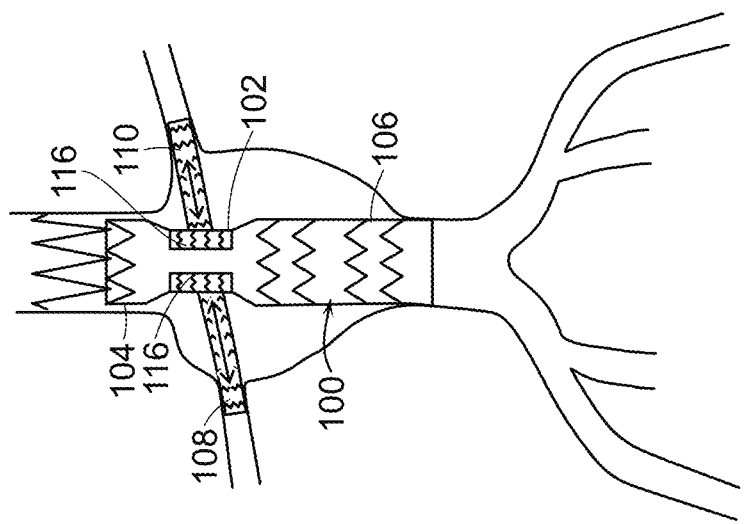
FIG. 5 is a side view of the thoraco-abdominal graft prosthesis of FIGS. 4A-4B, at an aneurysm site.
Figure 7:
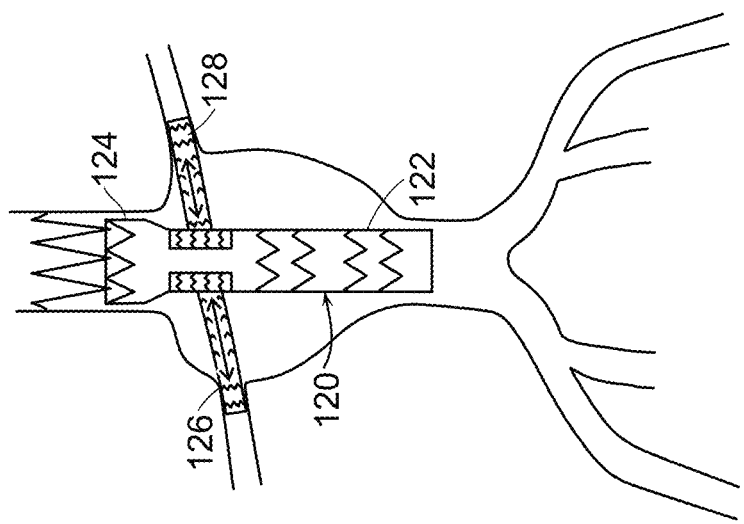
FIG. 7 is a side view of the embodiment of FIGS. 6A-6B at an aneurysm site.

At least one of tunnel graft proximal end 28 and tunnel graft distal end 30 of the at least one tunnel graft 50,54 is secured to main graft component 12, as shown in FIGS. 4, 5, 7. Tunnel grafts 50,52,54 are secured to main graft component 12 by, for example, a suture, bioadhesive material or another suitable material, as is known in the art.

In an embodiment, main tunnel graft component 12 can be bifurcated, as shown in FIGS. 1-3, or non-bifurcated, as shown in FIGS. 4A through 7.

In another embodiment, and referring to FIGS. 2 and 3, the invention is a method of implanting a thoraco-abdominal branch graft prosthesis 10, comprising the steps of delivering thoraco-abdominal branch graft prosthesis 10 through blood vessel 40 to thoraco-abdominal aneurysm site 42 in a patient. Thoraco-abdominal branch graft prosthesis 10 includes the components as set forth above with respect to FIG. 1. Main graft component 12 has luminal wall 14 defining an open proximal end 16, open distal end 18 opposite open proximal end 16. Main lumen 20 extends from open proximal end 16 to open distal end 18. At least one main graft wall fenestration 22 is defined by luminal wall 20. At least one tunnel graft component 20 has tunnel graft luminal wall 26 defining tunnel graft proximal end 28. Tunnel graft distal end 30 is opposite tunnel graft proximal end 28. Tunnel graft lumen 32 extends from tunnel graft proximal end 28 to tunnel graft distal end 30. At least one tunnel graft fenestration 34 is defined by tunnel graft luminal wall 26. Tunnel graft component 24 is within main graft lumen 20. Major longitudinal axis 36 of tunnel graft lumen 32 is substantially parallel to major longitudinal axis 38 of main graft lumen 20. Luminal wall 26 of tunnel graft component 24 is fixed to luminal wall 14 of main graft component 12, whereby fenestration 34 of tunnel graft luminal wall 26 is aligned with fenestration 22 of main graft luminal wall 14. At least one of tunnel graft main graft wall fenestration 22 is substantially aligned with at least one branch vessel 65 at the thoraco-abdominal aneurysm site.

At least one branch prosthesis 46 is inserted through at least one main graft wall fenestration 22 and at least one tunnel graft fenestration 34, and within the lumen of at least one tunnel graft component, the at least one branch prosthesis 46 having an open distal end 48 and an open proximal end 50; and the distal end 48 of the at least one branch prosthesis 46 is inserted into at least one branch vessel 65 at the thoraco-abdominal aneurysm site 42 (see, for example, FIG. 3). Branch prosthesis 46 can be inserted through main graft wall fenestration 22 either from within main graft component 12, or from outside main graft component 12.

The thoraco-abdominal branch graft prosthesis of the invention has the advantage of permitting access by the surgeon from a caudal or cranial position relative to the site of the thoraco-abdominal aneurysm (FIGS. 2, 3), thereby providing greater flexibility in a surgical approach depending upon the patient, site, degree of the aneurysm and morphology of the side branches. Tunnel graft component 24 of the main graft component 12 permits docking to secure a branch prosthesis (FIG. 3).

Figure 4B:
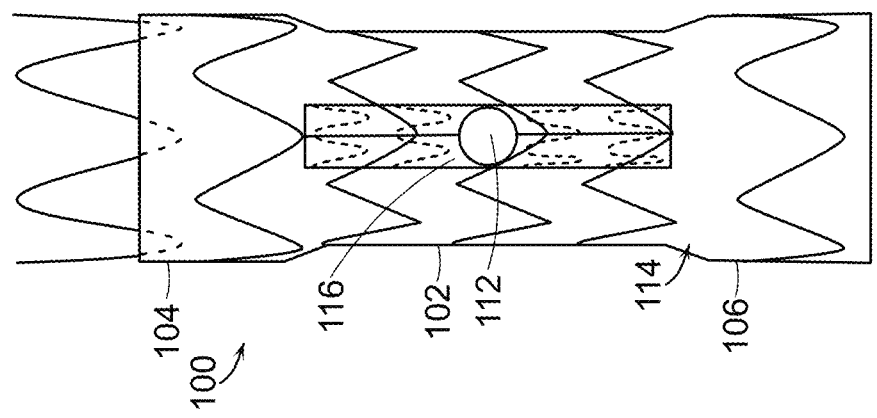
FIGS. 4A-4B are side views of one embodiment of a thoraco-abdominal graft prosthesis of the invention rotated 90° about a major longitudinal axis in sequence from FIG. 4A to 4B.
Figure 4A:
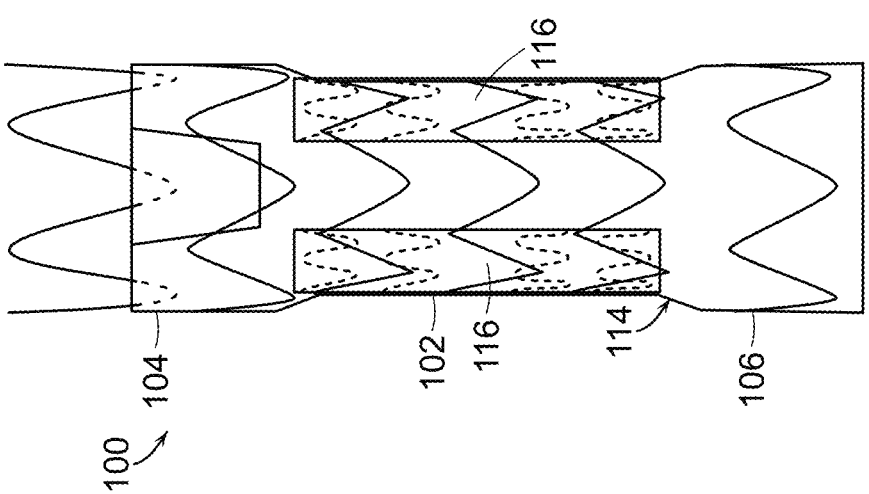

In another embodiment, shown in FIGS. 4A-B, and 5, main graft component 100 has midsection 102 having a diameter that is smaller than at least one of the end 104,106 of main graft component 100 to facilitate cannulation of the branch prosthesis. Narrower midsection 102 allows for more room to maneuver a guide wire or guide catheter through tunnel graft components 108,110 and main graft wall fenestration 112 in main graft wall 114 to tunnel grafts 116. Main graft component that includes a narrower midsection 102 can be bifurcated (not shown) or non-bifurcated (FIGS. 4A, 4B and 5). In the case of a branch graft prosthesis 100, such as a bifurcated graft prosthesis, a plurality of at least one end 104,106 includes a midsection 102 has a diameter that is smaller than at least one end 104,106.

Figure 6A:
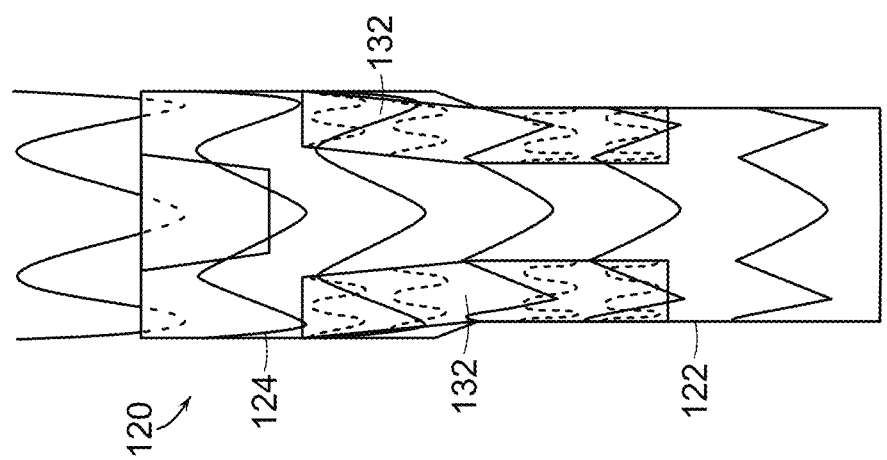
FIGS. 6A-6B are side views of yet another embodiment of the thoraco-abdominal graft prosthesis of the invention rotated 90° about a major longitudinal axis in sequence from FIG. 6A to FIG. 6B.
Figure 6B:
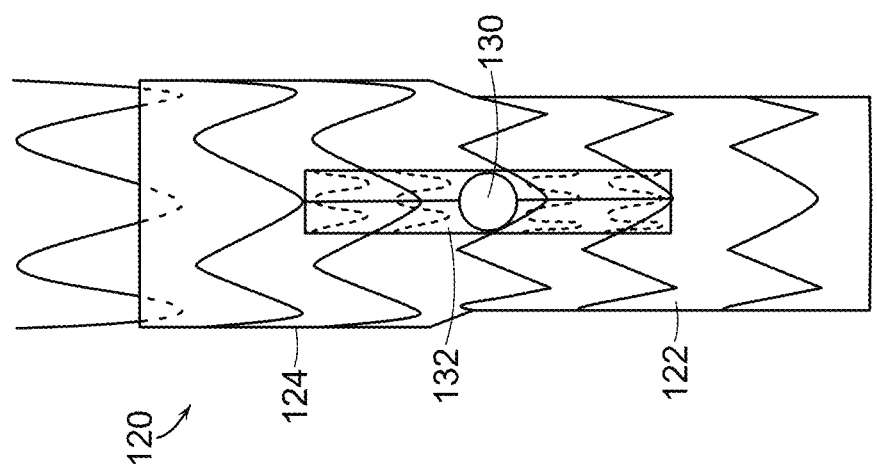

In yet another embodiment, shown in FIGS. 6A, 6B and 7, main graft component 120 includes tapered distal end 122 that has a smaller diameter than proximal end 124. This embodiment, like that shown in FIGS. 4A, 4B, and 5, has the advantage of facilitating cannulation of branch prostheses 126, 128 through main graft fenestrations 130 to tunnel graft 132. Main graft component that includes tapered distal end 122 that has a smaller diameter than proximal end 124, and which can be bifurcated (not shown) or non-bifurcated (FIGS. 6A, 6B and 7). In the case of a branch graft prosthesis 120, such as a bifurcated graft prosthesis, with a plurality of distal ends (not shown) tapered distal end 122 has a smaller diameter proximal to or at about the location of branching of the graft prosthesis.

Vascular repair devices of the invention can be implanted, for example, by transfemoral access. Additional vascular repair devices that are directed into the vascular repair devices of the invention can be implanted, for example, by supraaortic vessel access (e.g., through the brachial artery), or by transfemoral access or access from some other branch or branches of major blood vessels, including peripheral blood vessels.

The relevant teachings of all patents, published applications and references cited herein are incorporated by reference in their entirety. The relevant teachings of U.S. Pat. Nos. 8,292,943; 7,763,063; 8,308,790; 8,070,790; 8,740, 963; 8,007,605; 9,320,631; 8,062,349; 9,198,786; 8,062, 345; 9,561,124; 9,173,755; 8,449,595; 8,636,788; 9,333, 104; 9,408,734; 9,408,735; 8,500,792; 9,220,617; 9,364, 314; 9,101,506; 8,998,970; 9,554,929; 9,439,751 and U.S. patent application Ser. Nos. 14/226,005; 14/675,102; 15/099,974; 15/040,460; 14/575,673; 14/924,102; 15/166, 818; 15/167,055; 14/736,978; 13/454,447; 15/384,663; 13/788,724; 15/417,467; 15/230,601; 14/272,818 and 14/861,479 are also incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of implanting a thoraco-abdominal branch graft prosthesis, comprising the steps of:
    a) delivering a thoraco-abdominal branch graft prosthesis through a blood vessel to a thoraco-abdominal aneurysm site in a patient, the thoraco-abdominal branch graft prosthesis including
        i) a main graft component having a luminal wall defining, at least in part, an open proximal end, an open distal end opposite the open proximal end, a main lumen extending from the open proximal end to the open distal end, and at least one main graft wall fenestration, wherein the open distal end of the main graft component is tapered and has a smaller diameter than the proximal end of the main graft component; and
        ii) at least one tunnel graft component having a wall defining an open proximal end, an open distal end opposite the open proximal end, a lumen extending from the tunnel graft proximal end to the tunnel graft distal end, and at least one tunnel graft fenestration in the tunnel graft wall, wherein the tunnel graft component is within the main graft lumen and a major longitudinal axis of the tunnel graft lumen is substantially aligned with a major longitudinal axis of the main lumen, and wherein the wall of the tunnel graft component is fixed to the wall of the main graft component, whereby the fenestration of the tunnel graft wall is aligned with the fenestration of the main graft wall,
    wherein the at least one main graft wall fenestration is substantially aligned with at least one branch vessel of the patient at the thoraco-abdominal aneurysm site;
    b) inserting at least one branch prosthesis through the at least one main graft wall fenestration and the at least one tunnel graft fenestration within the lumen of the at least one tunnel graft component, the at least one branch prosthesis having an open distal end and an open proximal end; and
    c) inserting one of the distal end or the proximal end of the at least one branch prosthesis into at least one branch vessel of the patient at the thoraco-abdominal aneurysm site.

2. The method of claim 1, wherein the thoraco-abdominal branch graft prosthesis is a bifurcated thoraco-abdominal branch graft prosthesis.

3. The method of claim 1, wherein the at least one branch prosthesis is inserted through the at least one main graft wall fenestration and at least one tunnel graft fenestration from within at least one tunnel graft by an access point cranial to the thoraco-abdominal aneurysm site of the patient.

4. The method of claim 3, wherein the at least one branch prosthesis is inserted through the at least one main graft wall fenestration and at least one tunnel graft fenestration to within at least one tunnel graft by an access point caudal to the thoraco-abdominal aneurysm site of the patient.

5. The method of claim 1, wherein the luminal wall of the main graft component defines a midsection cross-sectional diameter of the main lumen that is smaller than at least one of the open proximal end and the open distal end of the main graft component.

6. The method of claim 1, wherein at one of the open proximal end and the open distal end of the at least one tunnel graft is secured to the main graft component, and wherein the wall of the tunnel graft component is fixed to the wall of the main graft component.

* * * * *